(12) United States Patent
Hellman et al.

(10) Patent No.: US 11,471,714 B2
(45) Date of Patent: Oct. 18, 2022

(54) NASAL DEVICE

(71) Applicant: NoseOption AB, Stockholm (SE)

(72) Inventors: Mikael Hellman, Stockholm (SE); Alexis Ruin, Stockholm (SE)

(73) Assignee: NoseOption AB, Stockholm (SE)

( * ) Notice: Subject to any disclaimer, the term of this patent is extended or adjusted under 35 U.S.C. 154(b) by 100 days.

(21) Appl. No.: 16/612,575

(22) PCT Filed: May 3, 2018

(86) PCT No.: PCT/EP2018/061324
§ 371 (c)(1),
(2) Date: Nov. 11, 2019

(87) PCT Pub. No.: WO2018/206388
PCT Pub. Date: Nov. 15, 2018

(65) Prior Publication Data
US 2020/0206547 A1    Jul. 2, 2020

(30) Foreign Application Priority Data

May 12, 2017    (SE) .................................... 1750584-3

(51) Int. Cl.
*A62B 23/06*    (2006.01)
(52) U.S. Cl.
CPC .................................... *A62B 23/06* (2013.01)
(58) Field of Classification Search
CPC .... A62B 7/00; A62B 7/10; A62B 9/00; A62B 9/06; A62B 18/00; A62B 23/00; A62B 23/06; A62B 23/02; A62B 23/025; A41D 13/11
See application file for complete search history.

(56) References Cited

U.S. PATENT DOCUMENTS

| | | | |
|---|---|---|---|
| 1,823,094 A | 9/1931 | Dylong | |
| 4,200,150 A | 4/1980 | Saadeh et al. | |
| 4,221,217 A * | 9/1980 | Amezcua | A62B 23/06 128/203.22 |
| 4,327,719 A | 5/1982 | Childers | |
| 5,425,359 A | 6/1995 | Liou | |
| 5,890,491 A * | 4/1999 | Rimkus | A62B 23/06 128/206.11 |
| D451,193 S | 11/2001 | McCormick | |

(Continued)

FOREIGN PATENT DOCUMENTS

| | | |
|---|---|---|
| CN | 2250782 Y | 4/1997 |
| CN | 2617418 Y | 5/2004 |

(Continued)

OTHER PUBLICATIONS

Swedish Search Report issued in SE 1750584-3, dated Dec. 4, 2017, 3 pages.

(Continued)

*Primary Examiner* — Colin W Stuart
(74) *Attorney, Agent, or Firm* — Sterne, Kessler, Goldstein & Fox P.L.L.C.

(57) ABSTRACT

A nasal device for filtering breathing air includes an elongated support member, and two rounded holder members, each arranged at a respective end of the elongated support member. The holder members are adapted to be inserted into a nostril with a distal end directed into the nostril, and a proximal end adjacent the nostril openings. The holder members include a bell-shaped cross-section in at least one plane in a distal-proximal extension.

17 Claims, 14 Drawing Sheets

(56) References Cited

U.S. PATENT DOCUMENTS

| | | | |
|---|---|---|---|
| 7,207,333 B2 | 4/2007 | Tohara | |
| 7,918,224 B2 * | 4/2011 | Dolezal | A62B 23/06 128/206.11 |
| 7,918,225 B2 * | 4/2011 | Dolezal | A62B 23/06 128/206.11 |
| 9,220,628 B2 * | 12/2015 | Bergstrand Borjegren | A61M 15/08 |
| 2003/0209145 A1 * | 11/2003 | Soper | A62B 23/06 95/273 |
| 2007/0227542 A1 * | 10/2007 | Kashmakov | A62B 23/06 128/206.11 |
| 2009/0007919 A1 | 1/2009 | Dolezal et al. | |
| 2014/0261459 A1 * | 9/2014 | Santelli, Jr. | A61L 2/0082 128/858 |
| 2015/0182766 A1 | 7/2015 | Dolezal et al. | |
| 2015/0238785 A1 * | 8/2015 | Chuang | A62B 23/06 128/202.27 |
| 2016/0256715 A1 | 9/2016 | Chao et al. | |
| 2016/0256716 A1 | 9/2016 | Lei | |

FOREIGN PATENT DOCUMENTS

| | | | |
|---|---|---|---|
| CN | 203417413 U | * | 2/2014 |
| CN | 203417413 U | | 2/2014 |
| CN | 204246706 U | | 4/2015 |
| CN | 105413081 A | | 3/2016 |
| DE | 88 04 725 U1 | | 5/1988 |
| DE | 201 01 539 U1 | | 6/2001 |
| FR | 1.211.911 A | | 3/1960 |
| JP | S59-184841 U | | 12/1984 |
| JP | 2014158968 A | | 9/2014 |
| WO | 99/11326 A1 | | 3/1999 |
| WO | 01/62342 A1 | | 8/2001 |
| WO | 2015/143344 A1 | | 9/2015 |

OTHER PUBLICATIONS

International Search Report and Written Opinion issued in PCT/EP2018/061324, dated Sep. 12, 2018, 15 pages.

Second Office Action issued in Application No. 201880038706.3, National Intellectual Property Administration, PRC, dated Apr. 21, 2021 (10 pages).

First Office Action issued in Application No. 201880038706.3, National Intellectual Property Administration, PRC, dated Sep. 3, 2020 (9 pages).

* cited by examiner

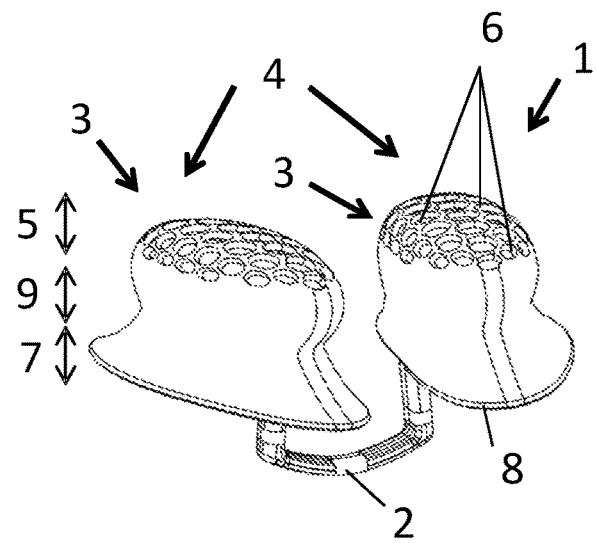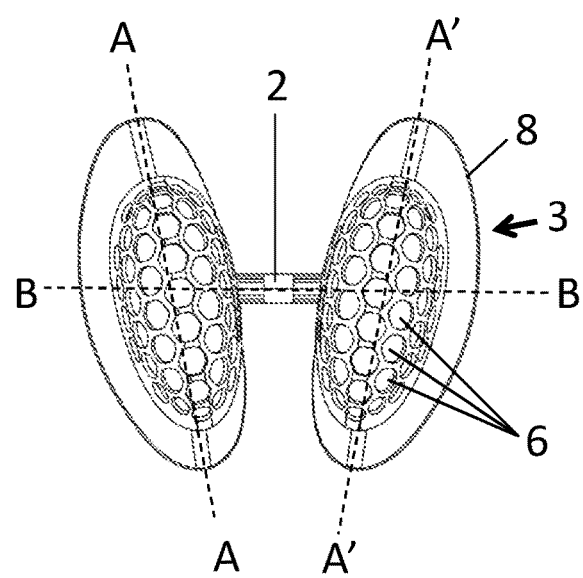
Fig. 1a            Fig. 1b
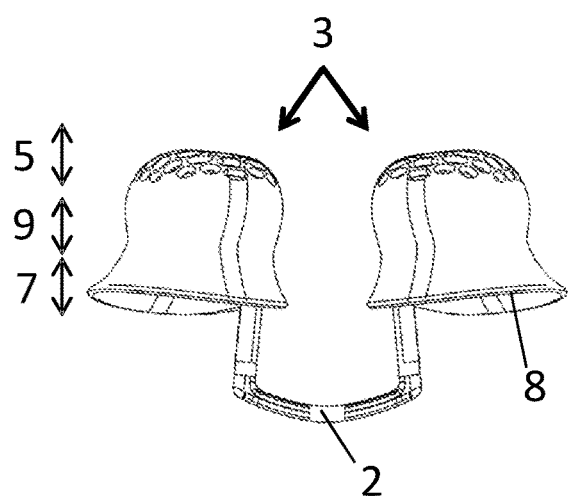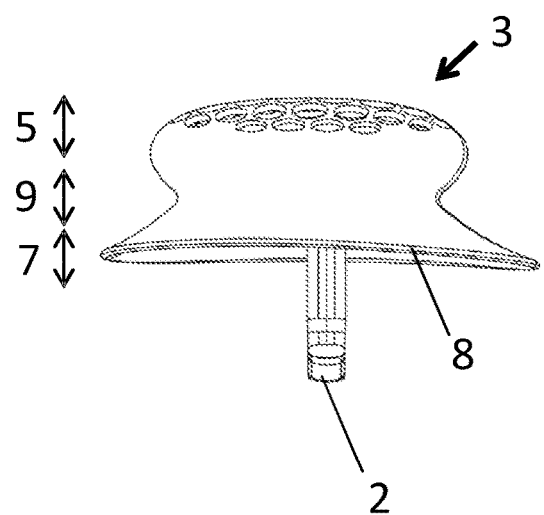
Fig. 1c            Fig. 1d

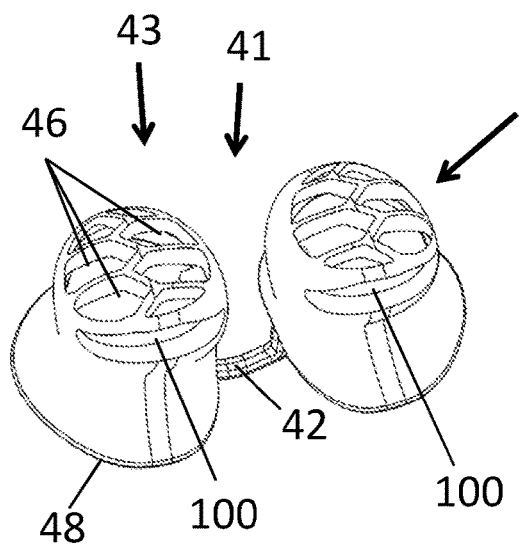
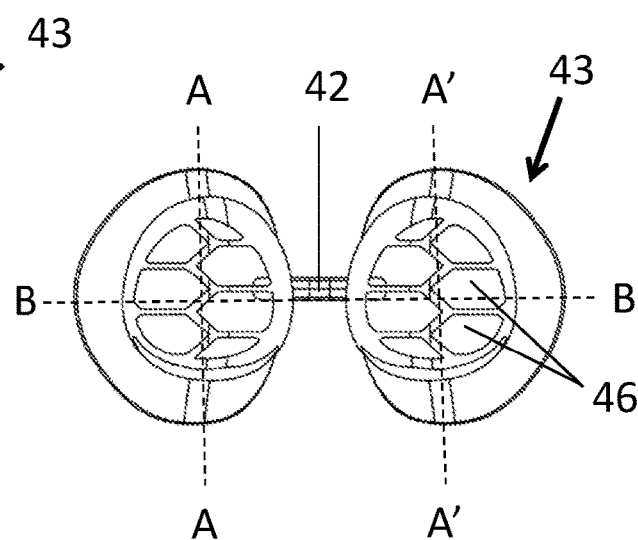
Fig. 3a  Fig. 3b
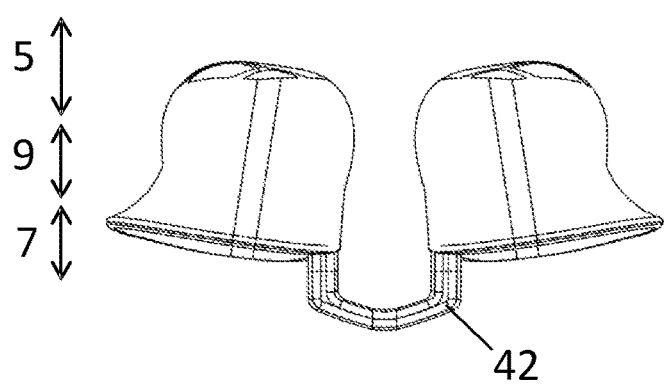
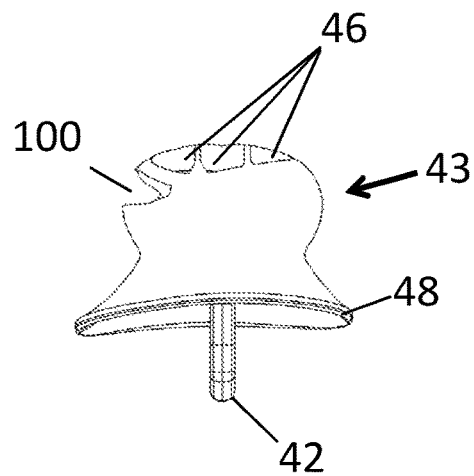
Fig. 3c  Fig. 3d

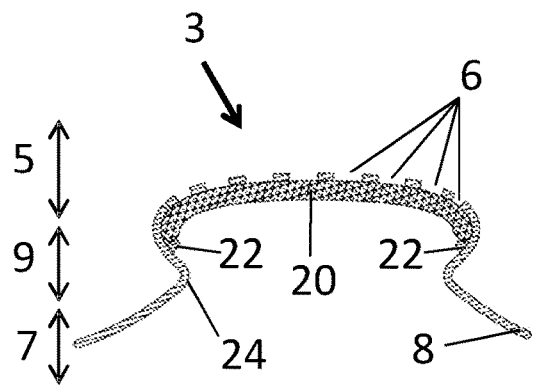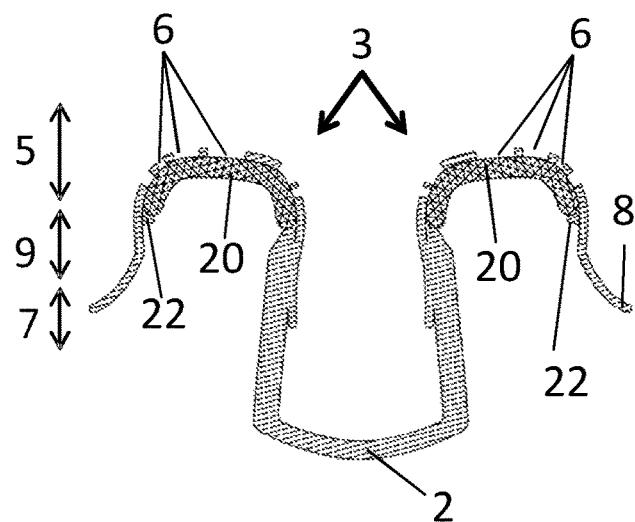
Fig. 6a　　　　　　　　Fig. 6b
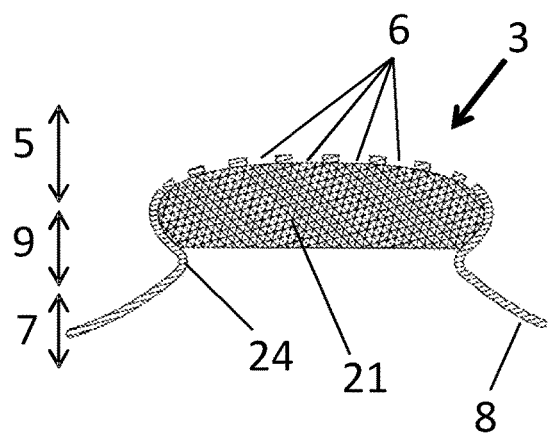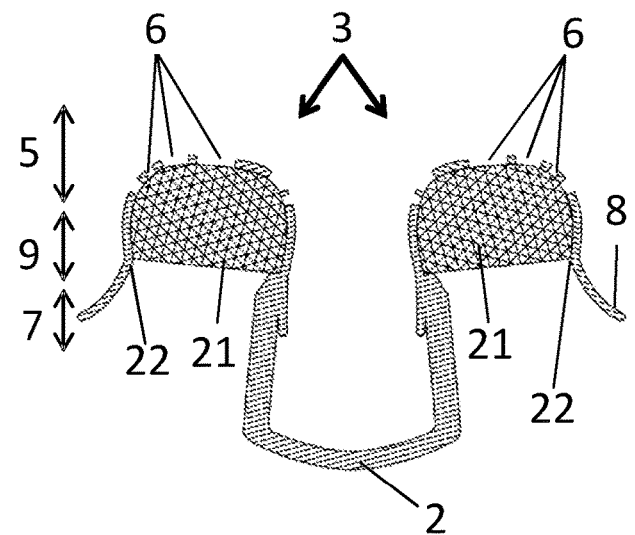
Fig. 7a　　　　　　　　Fig. 7b

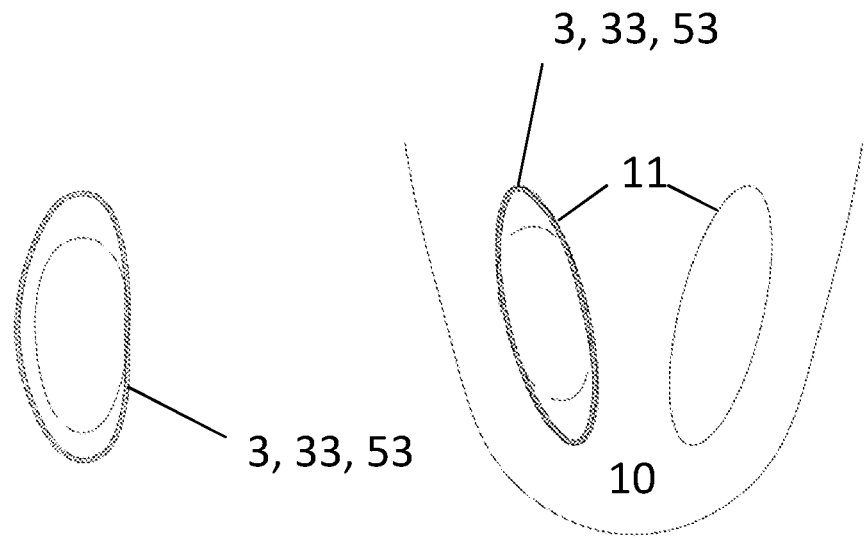
Fig. 9a
Fig. 9b
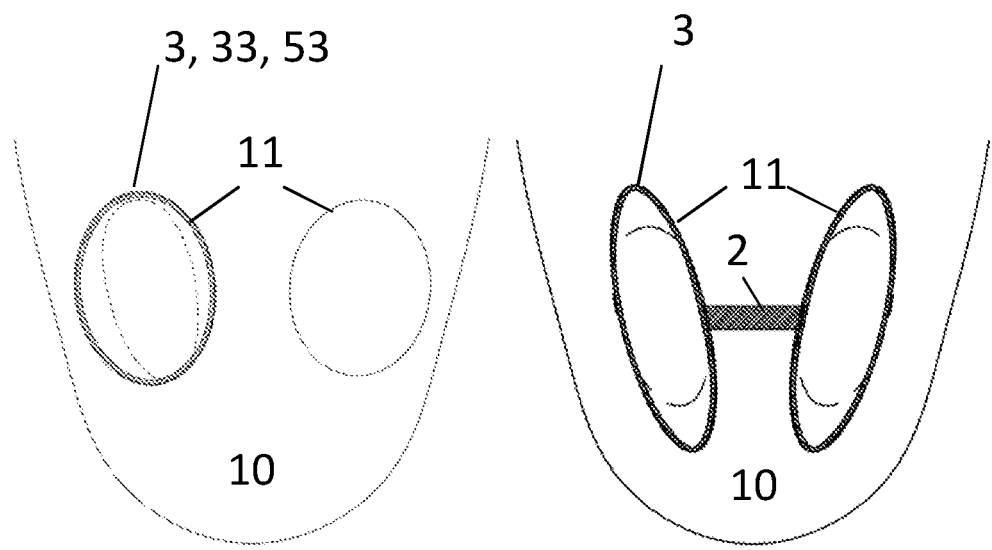
Fig. 9c
Fig. 9d

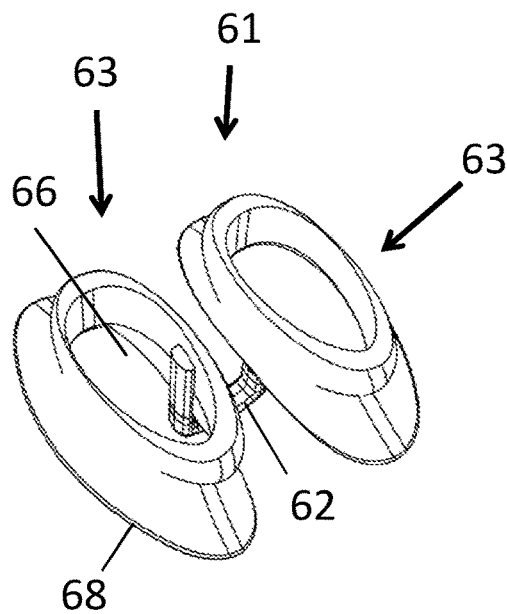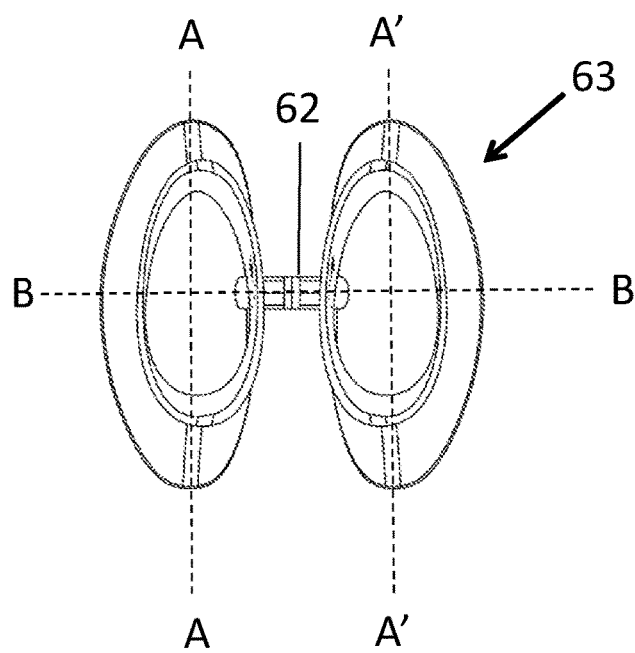
Fig. 11a　　　　　　　　　　Fig. 11b
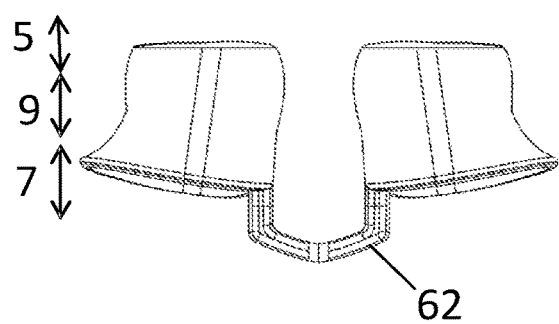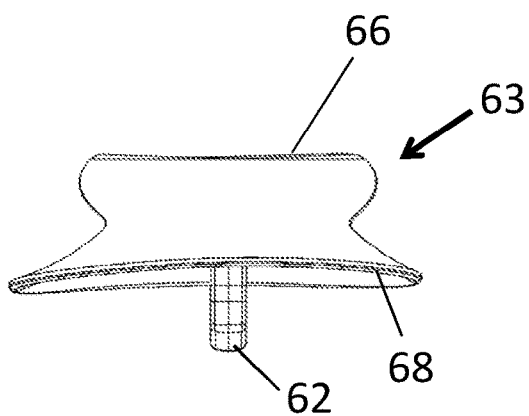
Fig. 11c　　　　　　　　　　Fig. 11d

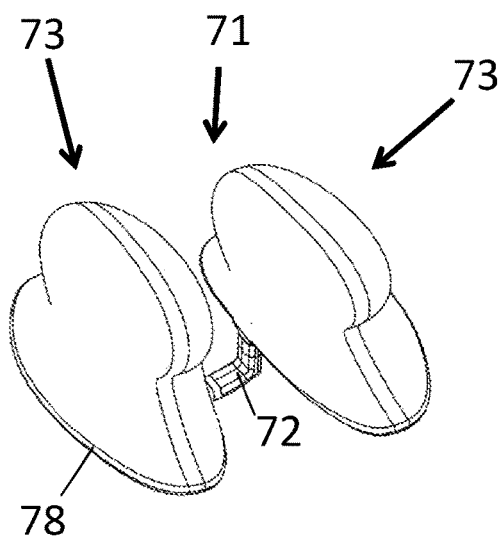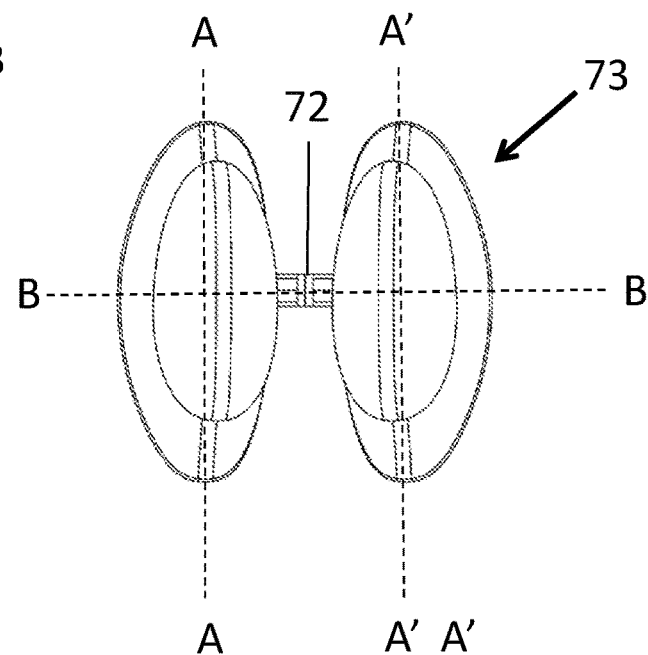
Fig. 12a
Fig. 12b
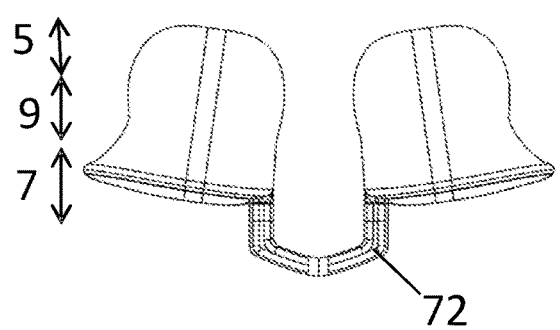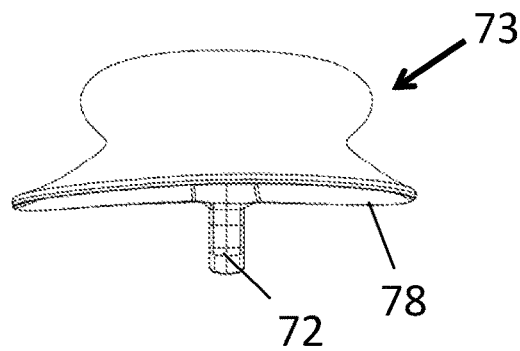
Fig. 12c
Fig. 12d

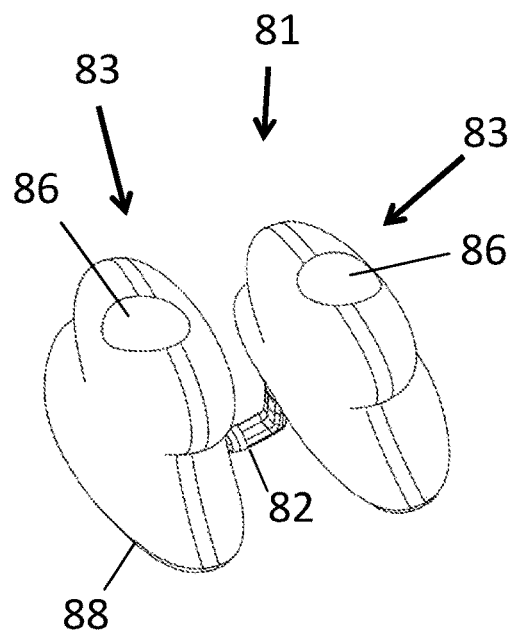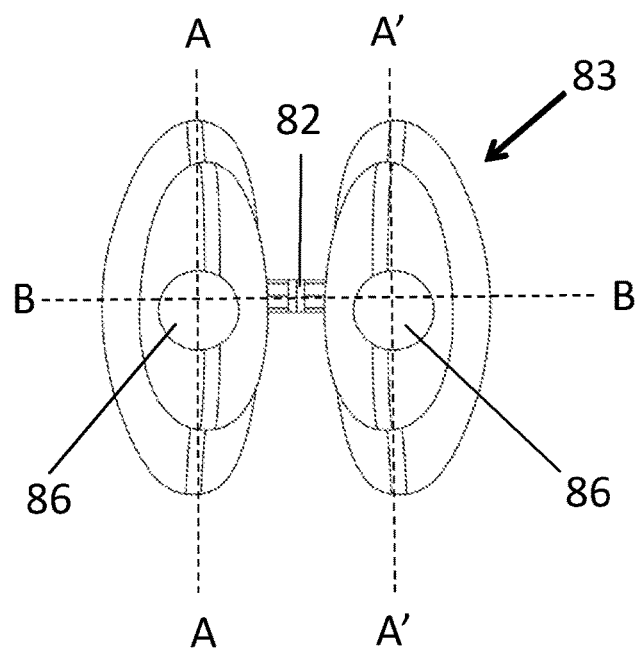
Fig. 13a
Fig. 13b
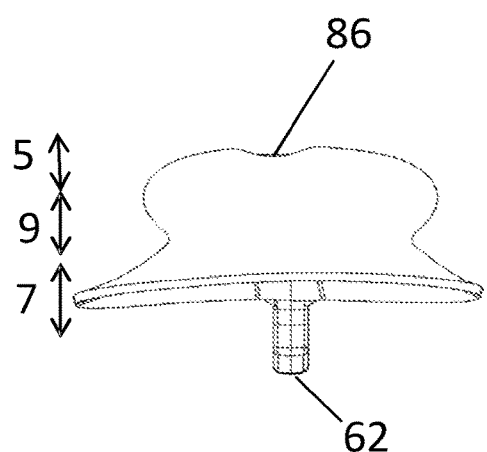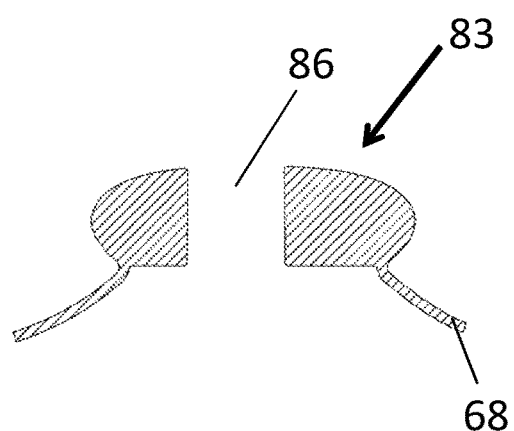
Fig. 13c
Fig. 13d

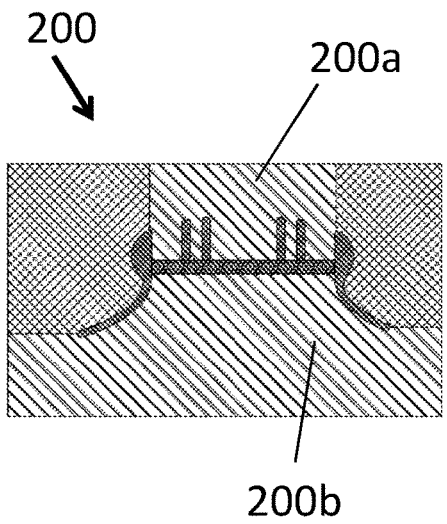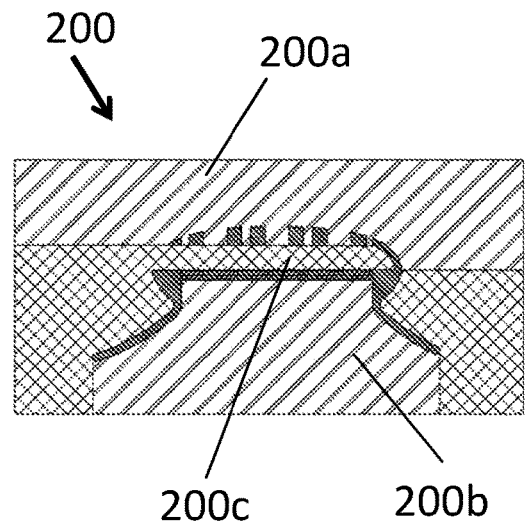
Fig. 14a  Fig. 14b
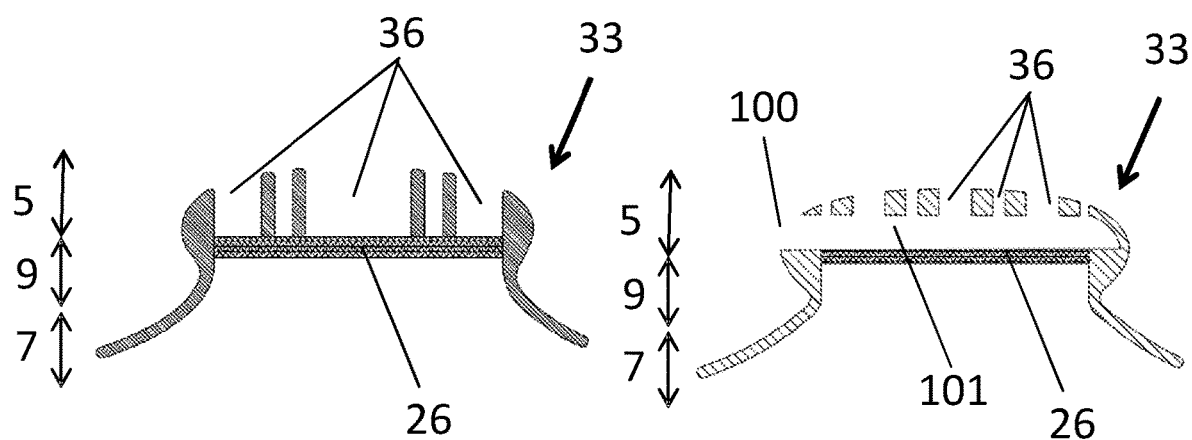
Fig. 15  Fig. 16

NASAL DEVICE

FIELD OF THE INVENTION

The present invention relates to a nasal device, according to the preamble of the independent claim.

BACKGROUND OF THE INVENTION

In many environments and situations there is a need to be able to purify, filter and/or de-odorize the air we breathe. For example, there are many situations where it is desirable to remove bad odour, such as in healthcare, military work, etc. In other situations a filter might be used to remove dust, pollen, gas, smog, odour or other harmful and/or irritating particles in the air we breathe. Many types of breathing or filtering devices exist, from face masks, to mouth covers and nose plugs. Many of these are bulky, uncomfortable and also un-aesthetic in that they alter the appearance. Furthermore, often such devices tend to be ineffective due to leakage of air.

An example of a nasal dust filter is described in U.S. Pat. No. 4,200,150, which discloses a nasal filter adapted to be inserted into the nasal passages and held in place by a clip applying tension to the septum walls. The filter includes a pair of umbrella-like round cups with a covered outside surface.

Another example is shown in U.S. Pat. No. 7,207,333, wherein is disclosed a nose clip with stopper-like end parts intended to be inserted into the nostrils. In one embodiment the stoppers each comprise a pair of round filters connected by a central axle.

US 2016/0256715 discloses yet another type of nose plug for filtering air. The device comprises an inner and an outer plug with a flip-lid, a filter sandwiched therebetween, and a nose clip. CN204246706U shows a nose plug with cup-shaped frames comprising inner grooves for holding a filter.

Further nose plugs for filtering air are shown in US 2015/0182766 wherein an air filtration device comprises two annular or cup-shaped support structures with concave-convex or planar filters, the support structures intended to be inserted into the nostrils and connected by a bridge.

The inventors of the present invention have identified a need for an improved nasal device, which provides for an improved fit and usability. Many of the known nose plugs cause irritation and discomfort due to friction between the plug and the inner surfaces of the nostrils. Others tend to be ineffective in sealing against air flow around each nose plug, thus making the device ineffective in filtering, guiding or hindering air.

SUMMARY OF THE INVENTION

An object of the present invention is to provide a nasal device which is comfortable to wear and discrete in appearance when used.

Another object of the present invention is to provide a nasal device that fits securely in a user's nostrils. Yet another object of the present disclosure is to provide a nasal device with minimal risk of irritating the nostrils.

A further object of the present invention is to provide a nasal device which, when provided with a filter, provides effective filtering of the air passing through the nose, and may be used for different types of situations, such as filtering pollen, dust, smog etc. YetP41706025EP00 another objective is to provide a nasal device which is cost-effective to manufacture.

The above-mentioned objects are achieved by the present invention according to the independent claim.

Preferred embodiments are set forth in the dependent claims.

In accordance with the present invention the nasal device for filtering breathing air comprises an elongated support member, and one or two rounded holder members, each arranged at a respective end of the elongated support member. The holder members are adapted to be inserted into a nostril with a distal end directed into the nostril, and a proximal end adjacent the nostril openings. The holder members are formed in one piece and made of a flexible material, and each comprise a bell-shaped cross-section in at least one plane in a distal-proximal extension. Further, the holder members each comprise a rounded distal portion, an open proximal portion comprising an outer rim disposed circumferentially around the outer perimeter of the proximal portion and extending radially outward from the holder member, and an intermediate waist portion arranged between the distal portion and the proximal portion. The intermediate portion has at least one outer circumference in a plane essentially transverse to a distal-proximal direction which is smaller than a respective largest outer circumference of each of the distal and proximal portions.

SHORT DESCRIPTION OF THE APPENDED DRAWINGS

FIGS. 1*a* to 1*d* illustrate various views of a nasal device.

FIGS. 2*a*-2*h* illustrate various views of another nasal device.

FIGS. 3*a*-3*d* illustrate various views of a further nasal device.

FIGS. 4*a*-4*d* illustrates a various views of yet another nasal device.

FIG. 5 illustrates schematically how a nasal device is adapted to be positioned in a nostril of a nose.

FIG. 6*a* illustrates a cross-sectional view of a nasal device as shown in FIG. 1*b* along the plane A-A or A'-A' further comprising an electrostatic filter member.

FIG. 6*b* illustrates a cross-sectional view of a nasal device as shown in FIG. 1*b* along the plane B-B further comprising an electrostatic filter member.

FIG. 7*a* shows a cross-sectional view of a nasal device as shown in FIG. 1*b* along the plane A-A or A'-A' further comprising a mechanical filter member.

FIG. 7*b* illustrates a cross-sectional view of a nasal device as shown in FIG. 1*b* along the plane B-B further comprising a mechanical filter member.

FIG. 8*a* illustrates a cross-sectional side view of a nasal device arranged in a nostril.

FIG. 8*b* illustrates a cross-sectional front view of a nasal device arranged in a nostril.

FIGS. 9*a*-9*c* are perspective views of a holder member of a nasal device seen from the underside of noses with differently shapes nostrils.

FIG. 9*d* is a perspective view of a nasal device seen from the underside of a nose.

FIGS. 10*a* and 10*b* illustrates a cross-sectional view of a nasal device as shown in FIG. 1*b* along the plane B-B.

FIGS. 11*a*-11*d* illustrate various views of a further nasal device.

FIGS. 12*a*-12*d* illustrate various views of another nasal device.

FIGS. 13*a*-13*d* illustrate various views of yet another nasal device.

FIGS. 14a and 14b illustrate two examples of a moulding tool and nasal device during manufacturing of a nasal device.

FIGS. 15 and 16 illustrate cross-sectional views of two different nasal devices.

DETAILED DESCRIPTION

Figure 2A:
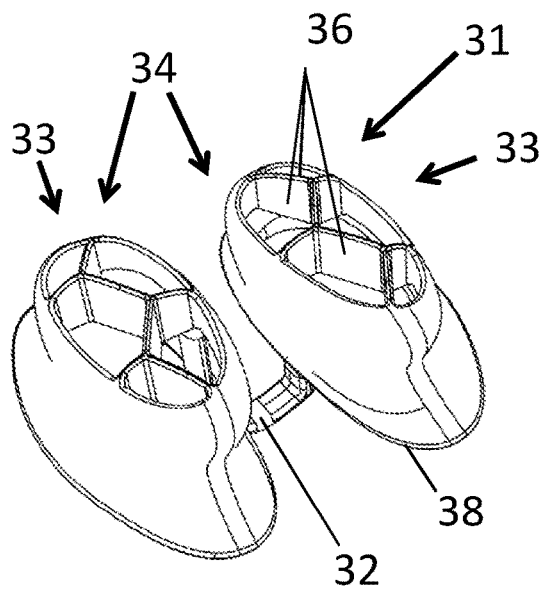

The present invention is a nasal device, for various uses, such as with an air filter, as a stopper, to administer a drug or other substance to a user, to facilitate breathing etc. The nasal device is designed such that it is small, convenient, and discrete, while at the same time providing effective sealing against the nostril opening with secure attachment and minimal irritation in the nostril.

In FIG. 1a is illustrated a first aspect of a nasal device in a general configuration when inserted into the nostrils. Specifically, the nasal device comprises a semi-rigid, elongated support member 2. At both ends of the support member 2, two rounded holder members 3 are provided, wherein the closed ends 4 of each of the rounded holder members are adapted to be inserted distally into a respective nostril. Correspondingly, the open end of each of the rounded holder members 3 is referred to as the proximal end, and is adapted to be arranged at the nostril openings, i.e. towards the outside of the nose, when inserted into the nostrils. FIG. 1b shows a nasal device as seen from a distal direction. The two indicated planes A and A', arranged in a generally proximal-distal direction, may be arranged in an angle relative to one another, as illustrated, or in a generally parallel manner, which will be further detailed below.

The support member 2 may initially be essentially straight and bendable such that the holders adapt the configuration shown in e.g. FIG. 1 when inserted into the nostrils. Thus, an initial configuration of a nasal device before use may be as showed in FIG. 1a, or may alternatively be in a configuration where the elongated support structure 2 is essentially straight and closed ends 4 of the two holder members 3 point essentially in opposite directions (not illustrated in the figures). An initial configuration may also be with the holder members 3 arranged in a parallel configuration when view from a distal direction, similar to the view shown in FIG. 2b, i.e. with the planes A and A' parallel to each other.

The support member 2 is preferably generally U-shaped, at least when the nasal device is inserted into the nostrils. The support member 2 may be adapted hold the holder members 3 in the general configuration of FIG. 1a, and may preferably also adapted to clip onto the nose septum in order to hold the nasal device in place during use. In many of the figures the support member 2 is shown as attached to an inside of the side wall of each holder member 3. However, the support member 2 may alternatively be attached to other positions of the holder member 3, such as adjacent to the proximal end, adjacent the inside of the distal end etc. As a further alternative, a support member may be integrally formed with the holder members, as will be described below in connection to FIGS. 4a-4d. FIGS. 2a-2h, 3a-3d and 4a-4d illustrate further nasal devices. These devices comprise many of the same features as those described for FIGS. 1a-1d, and it is understood that a nasal device may have any compatible combination of the features described. However, for illustrative purposes only a selected few variants are shown. Unless expressly detailed, similar features are understood to have similar functions.

FIGS. 2a-2d show a further nasal device 31 in perspective view, distal view, front view and side view, respectively. The nasal device 31 comprises a support member 32, two rounded holder members 33 with rounded distal ends 34, and an open proximal end, similar to the nasal device described above.

Figure 2B:
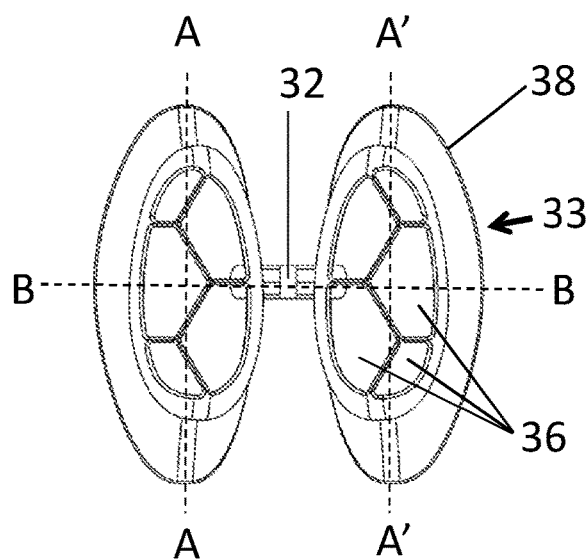
Figure 2C:
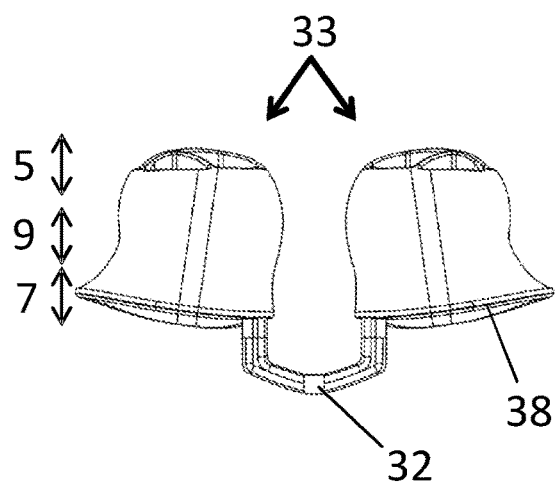
Figure 2D:
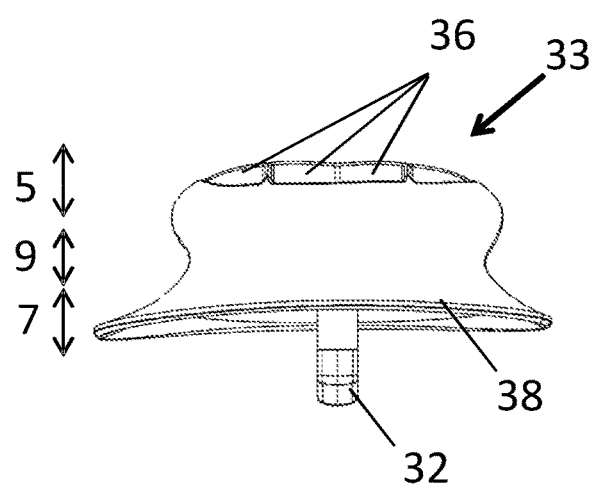
Figure 2E:
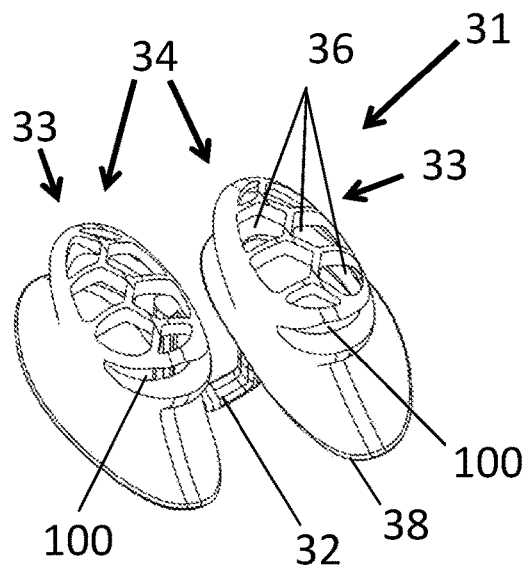

FIG. 2b shows a nasal device as seen from a distal direction. The two indicated planes A and A', arranged in a generally proximal-distal direction, may be arranged in an angle relative to one another, as disclosed above, or in a generally parallel manner, as illustrated in FIG. 2b.

FIGS. 2e-2h show another variation of a nasal device 31 in perspective view, distal view, front view and side view, respectively.

Figure 2F:
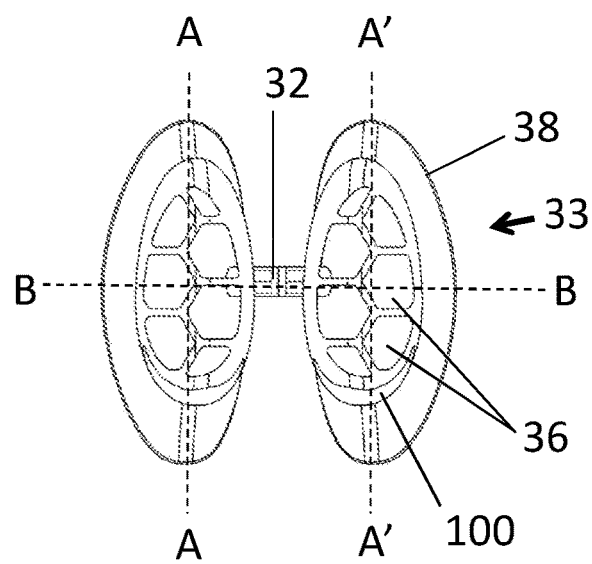
Figure 2G:
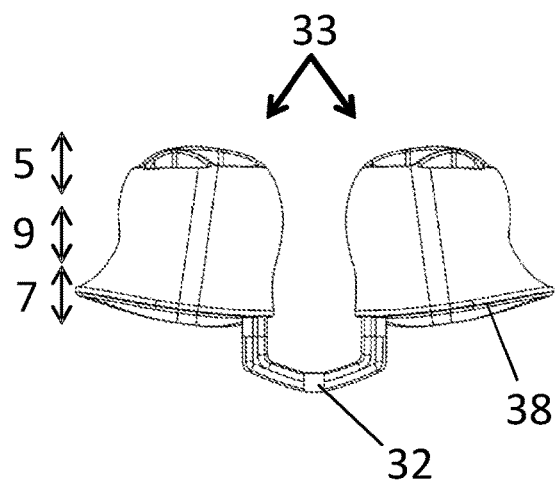
Figure 2H:
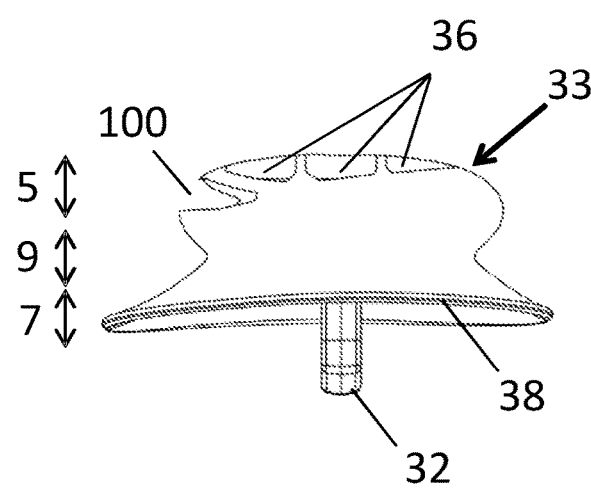

FIGS. 3a-3d illustrate a further similar nasal device 41, in perspective view, distal view, front view and side view, respectively. The nasal device 41 has an overall more rounded shape when viewed from a distal direction, as best seen in FIG. 3b, than that of the nasal device as seen in FIG. 1b, FIG. 2b or FIG. 2f. This aspect of the shape of the holder members will be further detailed below.

Figure 4A:
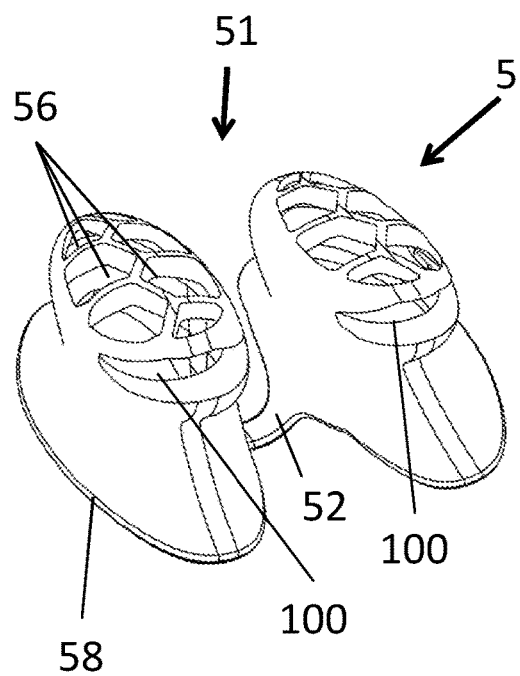
Figure 4B:
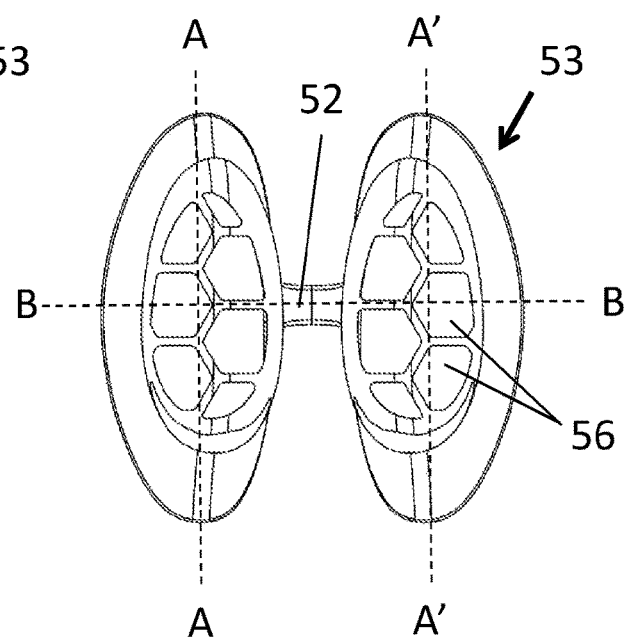
Figure 4C:
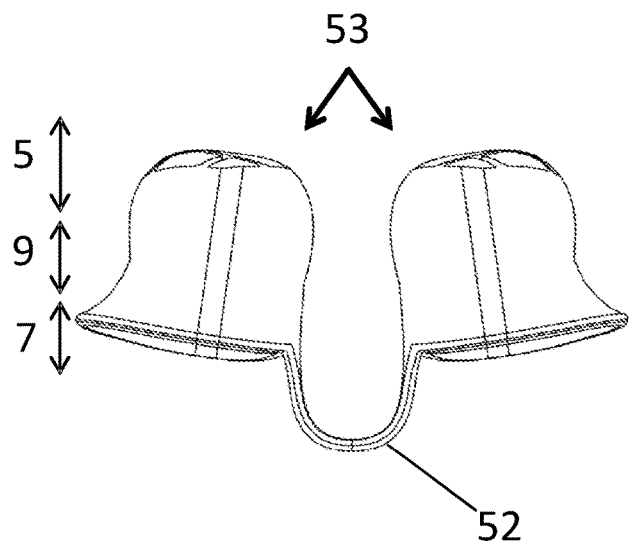
Figure 4D:
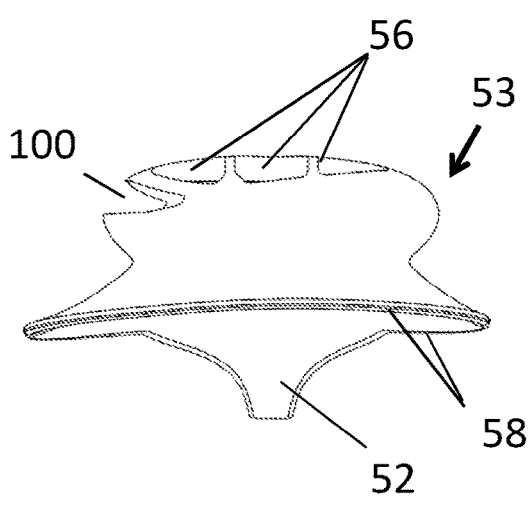

FIGS. 4a-4d illustrate another similar nasal device 51, in perspective view, distal view, front view and side view, respectively. Here the support member 52 is formed integrally with the holder member 53, specifically by extending part of a rim 58, on a side facing the other holder member 53, such that it forms the support member 52. Preferably, as seen in FIGS. 4c and 4d, an essentially flat extension of the outer rims 58 of two adjacent holder members 53 form a curved support member 52.

In one aspect, the holder members 3, 33, 43, 53 are preferably formed in one piece, and in another aspect, the two holder members and the support member 2, 32, 42, 52 are all moulded or formed as a single unitary member. The material of at least the holder members is preferably a biocompatible, flexible polymer. Non-limiting examples of material are silicone elastomers, thermoplastic elastomers (TPE), polyethylene (PE), polyethylene terephthalate (PET), polyvinylchloride (PVC), polyurethanes (PUR), fluoropolymers (PTFE, FEP, PFA, EFTE, ECTFE, PVDF), polyamide (PA), polypropylene (PP), polystyrene (PS), polylactic acid (PLA), polycarbonate (PC), polyetheretherketone (PEEK). Further, the material of the holder members 3 and/or the support member 2 may be a cellulose-based material, such as a starch-based material, for example polyactide (PLA) plastic, or polyhydroxyalkanoate (PHA) plastic. Optionally, the material may be a shape memory material (SMM), e.g. a shape memory polymer (SMP), for example.

Preferably, the material is a transparent or skin-colored material such that the nasal device is essentially invisible when applied in the nose. However, it is also conceivable that a material be chosen such that a nasal device has a contrasting color or specific pattern.

The support member may be strengthened by e.g. a metal wire core covered by the material above. A nasal device comprising such a strengthened support member might be useful to obtain a more secure fit in some applications.

Each of the holder members 3, 33, 43, 53 described in the different nasal devices above comprises a bell-shaped cross-section in at least one plane in a distal-proximal extension. As mentioned above, FIGS. 1a, 2a, 2e, 3a and 4a illustrate a perspective view of each of the nasal devices. Further, FIGS. 1c, 2c, 2g, 3c and 4c illustrates each nasal device from a front view, and FIGS. 1d, 2d, 2h, 3d and 4d illustrates the nasal device from a corresponding side view. These figures illustrate that the holder members 3, 33, 43, 53 have a generally rounded or bell-shaped profile, and may for illustrative purposes be seen as comprising three different integrally formed portions: a rounded distal portion 5, an open proximal portion 7, and an intermediate waist portion 9 arranged between the distal portion 5 and the proximal portion 7. The intermediate portion 9 forms a narrowing waist portion compared to at least the distal top portion 5. In other words, the intermediate portion 9 has at least one outer circumference in a plane essentially transverse to a distal-proximal direction which is smaller than a respective largest outer circumference of at least the distal portion 5. Preferably, the intermediate portion 9 also has at least one outer circumference in a plane essentially transverse to a distal-proximal direction which is smaller than a respective largest outer circumference of the proximal portion 7. This is seen in the figures as a narrowing middle portion 9 of the holder member 3, 33, 43, 53.

Figure 5:
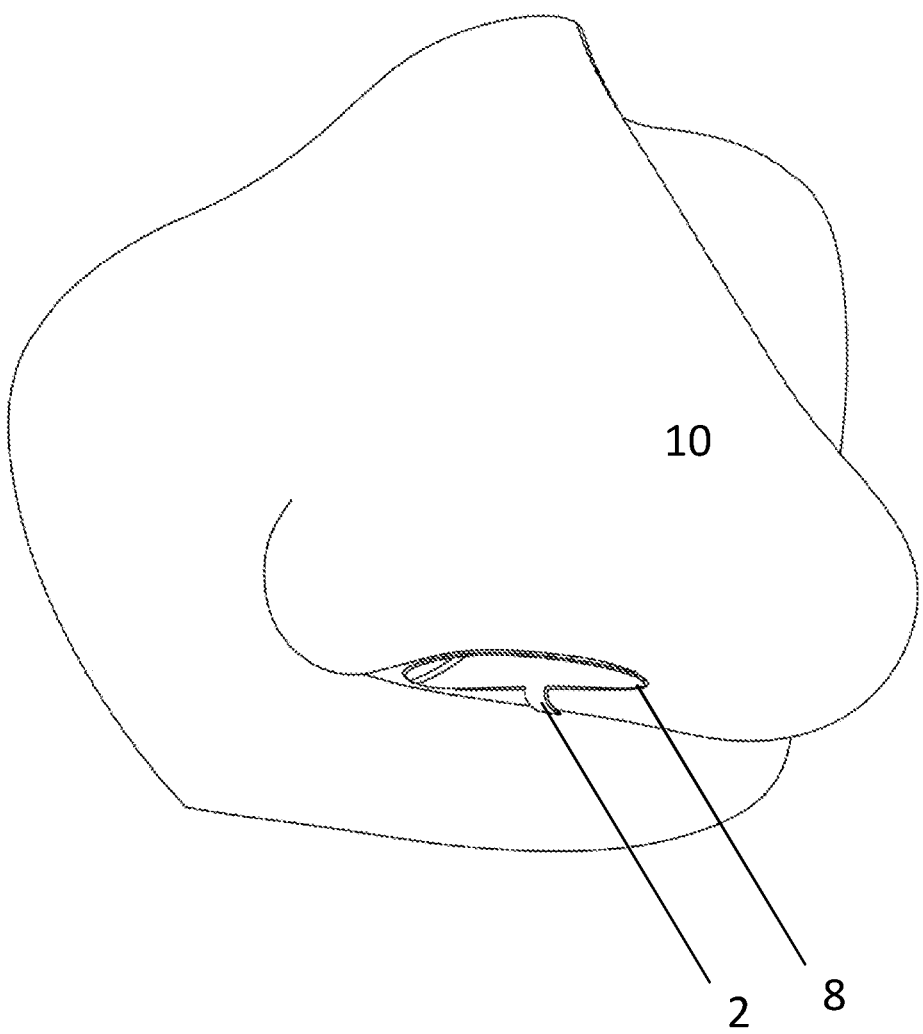

Further a flexible rim 8, 38, 48, 58 of the rounded holder member 3, 33, 43, 53, the rim being disposed circumferentially around the outer perimeter of the proximal portion 7, is adapted to protrude essentially radially outwards, such that the holder member 3, 38, 48, 58, and thus the nasal device 1, 31, 41, 51, seals tightly against the nostril opening. Preferably the rim 8, 38, 48, 58 is formed integrally in the proximal portion 7. In this manner, when the nose plug is inserted into the nostril opening, any air passing through the nasal device will be directed to pass essentially only through the holder member, if through-going holes are provided, as will be detailed further below. The rim enhances the sealing effect against the nostril opening of the overall profile of the holder member, such that the holder member is securely held in place in an essentially air-tight manner in the nostril opening. Further, preferably the rim will provide air-tight sealing of the outside of the nasal device against the nostril opening when the user inhales, due to the lowered air pressure in the nostrils. FIG. 5 shows a perspective view of a nasal device arranged in a nose 10, wherein it is seen that essentially only part of the support member 2, 32, 42, 52 and the rim 8, 38, 48, 58 of the proximal portion 7 are visible from the outside. One advantage of the narrowing profile of the intermediate portion 9 is that when arranged in a nostril opening, as illustrated in of FIG. 5, the holder member 3, 33, 43, 53 will be held effectively in place due to the narrowing middle section 9, as the wider distal portion 5 is arranged on the inside of the nostril opening and the rim 8 of the wider proximal portion 7 projects out of the nostril. Furthermore, the shape provides effective sealing against air passing through outside the holder member 3, 33, 43, 53, as the intermediate section 9 is well adapted to the general shape of the nostril. Further details of the adaptability will be described further below.

As mentioned, the nasal device is adapted for arrangement in the nostril openings. The shape of the holder members prevents the nasal device from penetrating further into the nostrils. Thus, the nasal device has minimal contact with the inner surfaces of the nostril, thus minimising the risk of irritating the nasal passages or causing discomfort. Furthermore, the nasal device will not impede the nostrils natural functions, such as warming and moistening inhaled air, and will also essentially avoid affecting or irritating the nasal hairs present on the inner surfaces of the nasal passages. In addition, the support member helps to hold the holder members in place. Thus, the combination of the bell-shaped profile and the protruding outer rim provides a comfortable and secure fit at the nostril opening, with minimal risk of irritation inside the nostril.

In one aspect, the distal surface of the rounded portion 5 may be provided with one or more through-going holes 6, 36, 46, 56 adapted to allow air to pass through said distal portion. Examples are seen in a distal view in FIGS. 1b, 2b, 2f, 3b and 4b. These through holes allow air to pass through the distal portion, and thereby from the inside to the outside of the nasal device, or vice versa. This allows air to flow freely through the nostrils when the nasal device is arranged in the nostril opening, and further may provide support for a filter member in the holder member, as will be described more in detail below. The set of through holes 6, 36, 46, 56 may be formed by a mesh structure, or multiple holes arranged in different patterns, such as, for example, but not limited to, honeycomb-shaped holes, flower petal-shaped holes, round holes, square or rectangular holes, elliptical holes, triangular holes. A few preferred structures are best seen in FIGS. 1b, 2b, 2f and 3b, which shows a distal view of the nasal device. The illustrated hole structures provides effective air flow due to a minimum of material between holes as well as a comfortable fit and rounded shape.

As an alternative, the rounded distal portion 5 may be provided with one larger through-going hole or no hole at all, as will be discussed in more detail further below.

In some aspects, the distal portion 5 of the holder member 33, 43, 53 may further comprise one or more through-going access holes 100 arranged essentially in a direction perpendicular to a distal-proximal extension. These access holes 100 are a result of a manufacturing method, which will be discussed in detail further below. However, these holes also provide further airflow through the nasal device when in use, as described for the distal through-going holes 6, 36, 46, 56 above.

As is also seen in e.g. FIGS. 1b, 2b and 2f, the holder members may each have a slightly oval or elliptical shape, or a more rounded shape, as seen in FIG. 3b. These shapes, combined with the slightly deformable/elastic material, provide the holder members 3, 33, 43, 53 with adaptability to different shapes of nostrils, thereby providing a wider range of use for a single size of a nasal device. This will be further detailed below.

Furthermore, the two holder members 3 are may be arranged in an angular manner in regard to each other, to conform to the orientation of two nostrils in relationship to each other. This is illustrated in FIG. 1b as the two planes A and A', which may be arranged in an angle within the range of 1 to 40 degrees, or within the range of 10-35 degrees, or within the range of 20-30 degrees relative to one another. However, the nasal device mat also be provided with the two holder members 3 arranged parallel to each other. This is illustrated in FIGS. 2b, 2f, 3b and 4b as the two planes A and A', which are preferably arranged essentially parallel to each other. Notably, during use, due to the use of a flexible material, the angle of the holder members relative to one another may be adjusted if needed when inserted into the user's nostrils.

The overall shape of the nasal device, and in particular the holder members 3, 33, 43, 53, provide a nasal device which is easy to use and apply in the nostrils of a user, and sits securely in the nostril opening. Further, the configuration permits effective breathing by a user when inserted into the nostrils, by only minimally inhibiting the air flow, for the nasal devices comprising through-going holes in the distal portion 5. In addition, the holder members 3 seal tightly against the nostril opening, especially when the user inhales. At the same time, the bell-shape of the holder members, with a narrowing waist section, allows the nasal device to effectively stay in place in the nostril openings during use.

The nasal device 1 as described above may be used together with a filter member, as will be detailed below. It may also be used with or as a stopper member, to prevent any flow of air at all through the member, e.g. for swimming purposes. It may also be used with other types of inserts or attachments, for e.g. treating the air flowing through a user's nostrils, which will be further detailed below.

FIGS. 6a and 7a illustrate a cross-sectional view of a nasal device as shown in FIG. 1b along the plane A-A or A'-A'. FIGS. 6b and 7b illustrate a cross-sectional view of a nasal device as shown in FIG. 1b along the plane B-B. The following applies also to any other nasal devices as described herein. As seen in FIGS. 6a, 6b, 7a, and 7b, the nasal device 1 may further comprise a filter member 20, 21, arranged against an inner surface of the distal portion 5 such that essentially all air passing through the nasal device 1 is directed through the filter. As described above, the distal portion comprises a set of through holes 6 for the air to pass through. In these figures, the filter is shown as being arranged against an inner surface of the distal portion 5. The filter may be held in place by inner protrusions, such as protrusions 22 shown in FIGS. 6a and 6b. These protrusions 22 may be continual (i.e. a rim) or intermittent around the inner circumference of the holder member 3. As seen in FIG. 6b, the filter member may also be arranged to rest against, or held in place by, the distal part of the support member 2. Further, a nasal device may correspondingly comprise a filter member 20, 21, arranged in the above manner against an inner surface of the distal portion 5 of a holder member as shown in any other holder member with through-going holes described herein, e.g. that of FIG. 2b, 2f, 3b, 4b, 11 b or 13b.

A filter member may also be arranged in other manners within the holder member, preferably within the distal portion 5. For instance, inner protrusions may be provided within the holder member, such that a filter member may be provided adjacent, or resting against, a proximal side of such protrusions. An example of such an arrangement will be described in connection with FIGS. 10 and 10b. Further, a filter member 26 may be integrally formed with the holder member, as will be described below.

The filter member 20, 21, 26 may be any type of air filter, including but not limited to, an electrostatic filter, a mechanical filter, a flimmer filter, a submicron filter, or a nanofilter. The filter member may be adapted to filter out particulate contaminants, different types of dust or biological contaminants. More specifically, the filter member may be adapted to capture soot, tobacco smoke, oil smoke, fly ash, cement dust, suspended atmospheric dust, heavy dust, sand, smog, pollution, oil mist, tobacco smoke or dust, metallurgic dust, pesticides, gaseous molecules, allergens such as animal allergens or house dust mite allergens, mould spores, pollen, chemical vapours, odours etc. There may also be a need to protect a user against airborne diseases, and a filter member may be provided to filter out bacteria, viruses or pathogens of other types. The filter member 20, 21, 26 may be adapted to filter particles of a size range of 0.01 nanometer in diameter and larger. FIGS. 6a and 6b illustrate the nasal device with a thin type of filter 20, such as an electrostatic filter. FIGS. 7a and 7b illustrate the nasal device with a thicker or more three-dimensional filter 21, such as a mechanical filter. Notably, a nasal device may be used with two or more filter members at the same time, of the same or different types. Two or more filter members may also be used interchangeably over time. A nasal device may also be used with a filter member or other member made of a suitable material adapted to either humidify or dehumidify the air breathed in by the user.

In some aspects, the filter member 20, 21 comprises a flexible material, which is adaptable to the inner shape of the holder member. Further, the filter member 20, 21 is may be provided in an overall oval or elliptical shape, to match the inner shape of the holder member 3. In some aspects, the filter may be formed by laser cutting or other cutting techniques. In some aspects, a cutting technique causing stiffened or hard edges of the filter 20, 21 may be used, which might provide a better fit inside the holder member 3.

An advantage of the rounded distal shape of the holder members 3, and any filter placed therein, is that the surface area exposed to breathing air is increased compared to using a flat filter surface. This provides enhanced filtering of the air passing through the nasal device 1, while not impeding breathing capacity of the user.

In one aspect, the filter member 20, 21 is held in place by the narrowing intermediate portion 9, essentially forming an inner circumferential rim 24 extending radially inwards at the middle portion 9. The narrowing intermediate portion 9 preferably works in combination with a press-fit arrangement of the filter member 20, 21 in the holder member 3, to hold the filter member 20, 21 in place.

Figure 10A:
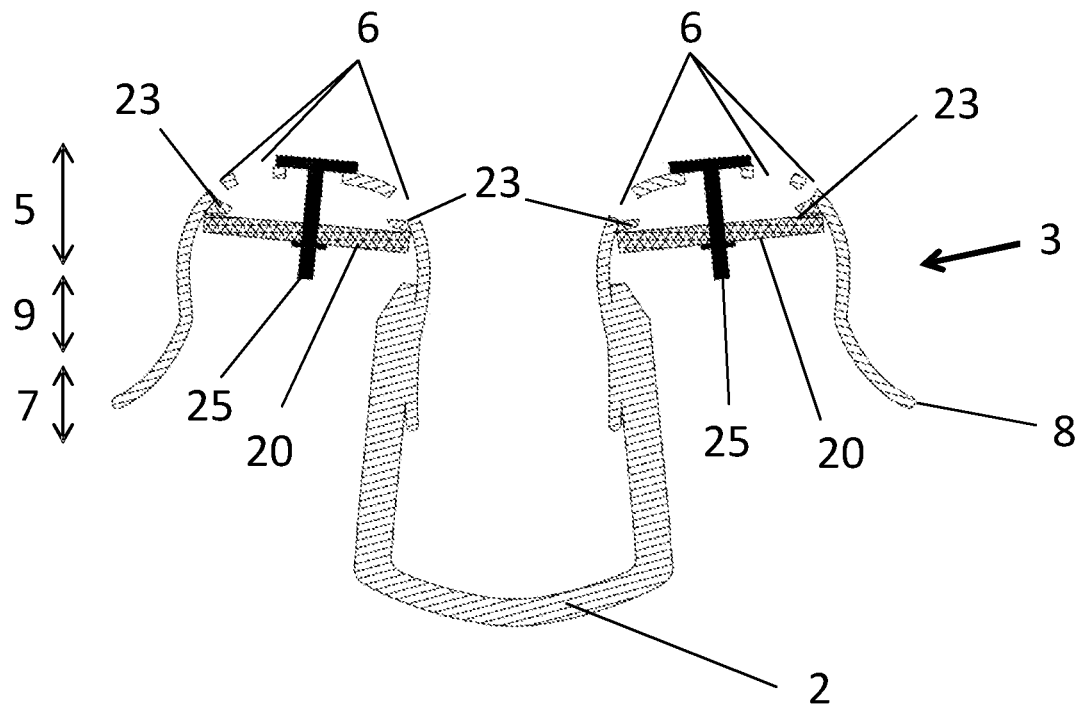
Figure 10B:
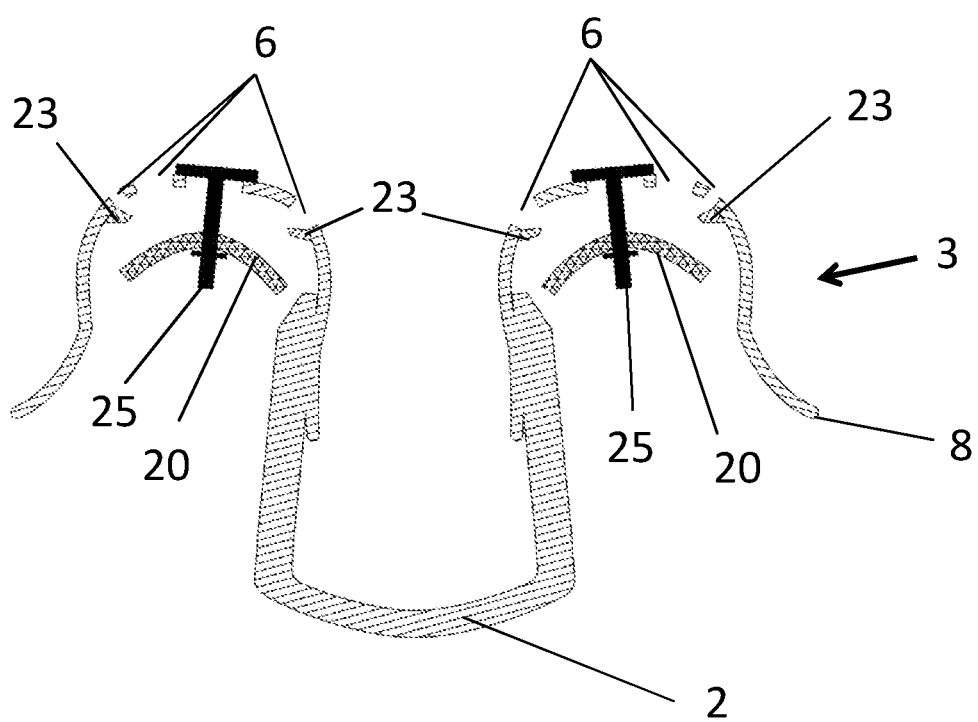

In another aspect, the filter member 20, 21 is held in place by an attachment member. An attachment member may be any of the non-restricting examples of a pin, a thread, glue or adhesive, a frame or holder, or an extension of the support member 2. The filter member may be attached in such a manner as to allow at least part of the filter member to freely move when air is exhaled, in essence functioning as a check valve. In such an arrangement, the filter member may be arranged such that all air passing through the nasal device is directed through the filter member when the user inhales, ensuring effective filtering of the inhaled air. When the user exhales at least some of the air is allowed to pass around or outside the filter member. Any arrangement fulfilling these criteria may be used. As an example, the filter member may be arranged such that it is pressed tightly against the inner surface of the holder member when a user inhales, and adapted to be more loosely arranged when the user exhales. Another example is shown in FIGS. 10a and 10b. Similar to the nasal device shown in FIGS. 6b and 7b, FIGS. 10a and 10b illustrate a cross-sectional view of a nasal device as shown in FIG. 1b along the plane B-B. However, the below may be applied in any other holder member with through-going holes described herein, e.g. that of FIG. 2b, 2f, 3b, 4b, 11 b or 13b.

As described above, the nasal device 1 further comprise a filter member 20. Herein, the filter member is held in place with a pin 25, attached at a distal end of the pin 25 to the distal end of the holder member 3 and at the proximal end of the pin 25, attached to filter member 20. FIG. 10a illustrates an initial state, as well as the configuration when a user, having applied the nasal device in the nostrils, inhales, wherein the filter member 20 rests against protrusions 23 arranged around the inside of the distal end of the holder member 3. All air passing into the nostrils will thus pass through the filter member 20. However, as shown in FIG. 10b, when the user exhales, the air passing through in a proximal direction will press the edges of the filter member 20 away from the protrusions 23, allowing air to pass both through the filter member 20, but also around the filter member 20.

Some users may feel an enhanced breathing ability using such a check valve arrangement.

Figure 8A:
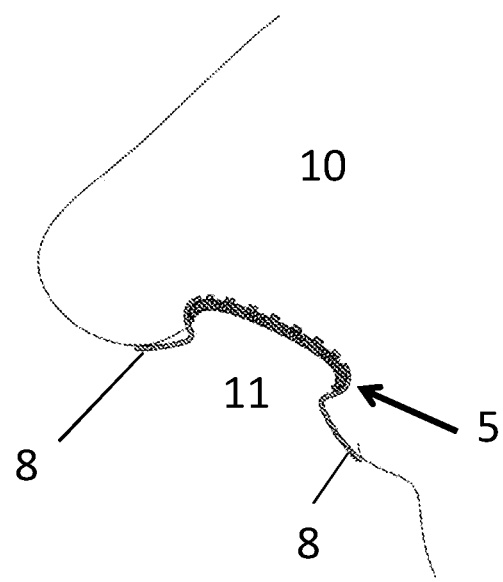
Figure 8B:
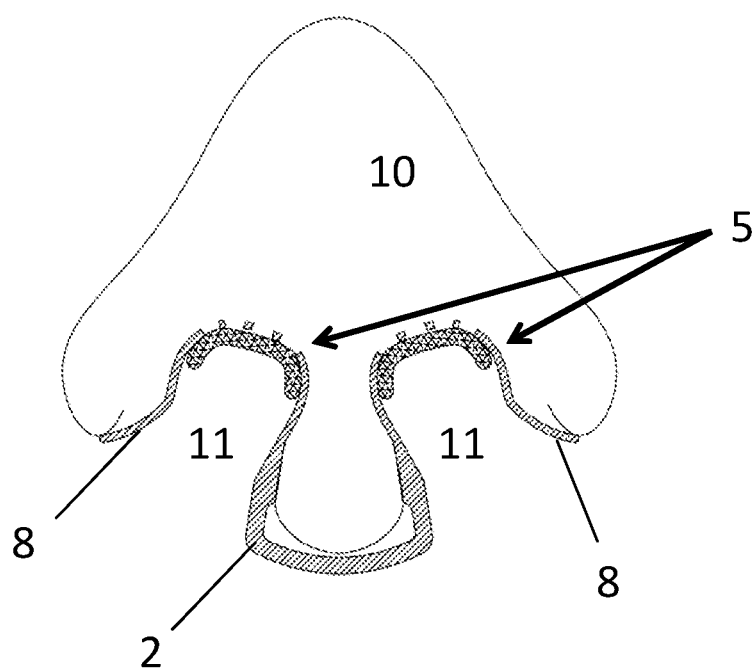

To further illustrate how a nasal device according to any aspect as disclosed herein is advantageously adapted to fit in the nostril openings, FIG. 8a show a cross-sectional side view of the nasal device shown in FIGS. 6a and 6b. FIG. 8b shows the nasal device in a cross-sectional front view. Each holder member 3 fits into a nostril opening 11 of a nose 10 such that the wider distal end 5 is arranged inside the nostril, and the proximal portion, and especially the rim 8, is arranged protruding outward from the nostril. In FIG. 8b it is further seen that the support member 2 provides further securement of the nasal device to the nose and in the nostrils.

FIGS. 9a-9d further illustrate the adaptability of the nasal device, and in particular of the holder members 3, 33, 43, 53, to differently shaped nostrils. These figures show perspective views as seen from the underside of a nose, i.e. from a proximal direction. Even though a nasal device may be provided in different oval or round shapes, examples of which may be seen in FIGS. 1a, 2a and 3a, the adaptability of the shape of the nasal device minimises the need to provide many different sizes and shapes of the nasal device. FIG. 9a shows the initial shape of an oval holder member of a nasal device, e.g. as shown in FIG. 1a, 2a or 2f. FIG. 9b shows the same holder member when inserted into a nostril 11 having an oblong shape. FIG. 9c shows the same holder member when inserted into a nostril 11 having a rounded shape. The shape of the holder member, in combination with it being made of a deformable and flexible material, allows it to adapt to essentially any nostril shape. A user may for example squeeze the holder members slightly in any direction to easily adapt the shape as needed. FIG. 9d shows a nasal device with two holder members 3 and a support member 2 from the same view.

In some aspects, the support member, as described in any of the nasal devices above, may be adjustable in length (not illustrated in the figures), such that the nasal device is more adaptable to different sizes and shapes of noses and nostrils. The support member may also be provided in several different pre-set lengths.

FIGS. 11a-11d, 12a-12d and 13a-13d illustrate further nasal devices. These devices comprise many of the same features as those described for FIGS. 1-4, and it is understood that a nasal device may have any compatible combination of the features described. However, for illustrative purposes only a selected few variants are shown. Unless expressly detailed, similar features are understood to have similar functions. Notably, all nasal devices described herein comprise holder members with a cross-sectional bell shape, and will thus all provide a secure and comfortable fit in the nostril opening, as shown in e.g. FIGS. 5, 8a, 8b and 9d.

FIGS. 11a-11d show another nasal device 61 in perspective view, distal view, front view and side view, respectively. The nasal device 61 comprises a support member 62, two rounded holder members 63, and an open proximal end 7. A rim 68 is disposed circumferentially around the outer perimeter of the proximal portion 7, similar to the nasal devices described above. However, in this nasal device one single large through-going hole 66 is provided at the distal end 5.

FIG. 11b shows a nasal device 61 as seen from a distal direction. The two indicated planes A and A', arranged in a generally proximal-distal direction, may be arranged in an angle relative to one another, as disclosed above, or in a generally parallel manner, as illustrated in FIG. 11b.

A nasal device as shown in FIG. 11 may be used as a nostril expander, and may as such provide enhanced ability to breathe through the nose. This may be especially useful for a user with small or tight nostrils, either naturally occurring or as a result of obstruction or trauma.

A nasal device as illustrated in FIG. 11 may also be provided with a filter member, according to any compatible aspect described herein, including a filter member whose edges are integrated or molded into the sides of the holder member. A filter member may thus be arranged to filter all air passing through the holder member, or a selected part of the air, or air only in one direction.

FIGS. 12a-12d show a further nasal device 71 in perspective view, distal view, front view and side view, respectively. The nasal device 71 comprises a support member 72, two rounded holder members 73, and an open proximal end. A rim 78 is disposed circumferentially around the outer perimeter of the proximal portion 7, similar to the nasal devices described above. However, this nasal differs from the previously described nasal devices in that it has a closed distal end 5. Thus, when used it will act as a stopper in the nostril. Notably, a stopper member may also be formed by providing a blocking member in this nasal device, for further support, or in any of the nasal devices described herein. The stopper nasal device may be useful when breathing or passage through the nose is not desired. This could be during water sports or other activities in water. It could also be used in medical situations, to force or encourage the user to breathe through the mouth, rather than through the nose, such as when administering drugs etc.

The two indicated planes A and A', arranged in a generally proximal-distal direction, may be arranged in an angle relative to one another, as disclosed above, or in a generally parallel manner, as illustrated in FIG. 12b.

FIGS. 13a-13c show yet another nasal device 81 in perspective view, distal view, and side view, respectively. The nasal device 81 comprises a support member 82, two rounded holder members 83, and an open proximal end. A rim 88 is disposed circumferentially around the outer perimeter of the proximal portion 7, similar to the nasal devices described above. At least one of the holder members 83 is provided with one larger through-going hole 86. FIG. 13d shows a cross-sectional view along the line A or A' in FIG. 13b, in which it is seen that the holder member 83 may be provided as essentially solid piece of material at the distal end, with a through-going hole 86, such that air may pass through the holder member via the hole 86. In such a nasal device the holder member 86 and through-going hole 86 may be adapted for attachment of a tube or coupling member. Such adaption for attachment may e.g. be via an integrated connection, or via press-fit, a Luer-lock, a snap-lock or a threaded screw member. Conceivably, such a nasal device is useful for administering oxygen or other gases, anaesthetics, drugs, or other substances suitable for nasal administration. Other examples of use is to administer water, saline or other substances to cleanse and/or hydrate the nostril.

In FIGS. 13a and 13b both the holder members 83 are provided with a through-going hole 86. However, it is also possible to provide a nasal device with one holder member 83 as seen in FIG. 13 and one holder member 73 as seen in e.g. FIG. 12, i.e. one holder member with a through-going hole and one holder member in the form of a stopper member. This is useful to enhance administration of a substance in one nostril, as the tube would be connected to one nostril, while the other nostril is stoppered.

Even though each nasal device disclosed herein is illustrated as having two holder members of the same type, it is also conceived to combine two different types of holder members 3, 33, 43, 53, 63, 73, 83 with each other in a single nasal device. One example is described above, with a stoppered holder member 73 combined with a holder member 83 adapted for attachment of a tube. Another example may be a nasal device with a holder member 83 adapted for attachment of a tube combined with holder member 3, 33, 43 provided with a filter member 20, 21 for filtering air while simultaneously administering a substance, e.g. oxygen or anaesthesia through a tube. A further example is to combine holder members with different sizes and/or shapes, in order to adapt to situations where the two nostrils are different sizes or shapes. Yet another example is the use of only one holder member with a support member, such that the single holder member may be secured further by the support member, which is then clipped onto the nostril septum.

Notably, similar to the holder members described for FIGS. 1 through 10, the holder members shown in FIGS. 11, 12 and 13 have a generally rounded or bell-shaped profile, and may for illustrative purposes be seen as comprising three different integrally formed portions: a rounded distal portion 5, an open proximal portion 7, and an intermediate waist portion 9 arranged between the distal portion 5 and the proximal portion 7. The intermediate portion 9 forms a narrowing waist portion compared to at least the distal top portion 5. Thus, the intermediate portion 9 has at least one outer circumference in a plane essentially transverse to a distal-proximal direction which is smaller than a respective largest outer circumference of at least the distal portion 5. Preferably, the intermediate portion 9 also has at least one outer circumference in a plane essentially transverse to a distal-proximal direction which is smaller than a respective largest outer circumference of the proximal portion 7. This is seen in the figures as a narrowing middle portion 9 of the holder member 63, 73, 83.

Further the flexible rim 68, 78, 88 is adapted to protrude essentially radially outwards, such that the holder member 63, 73, 83, and thus the nasal device 33, 43, 53, seals tightly against the nostril opening. Preferably the rim 68, 78, 88 is formed integrally in the proximal portion 7. The rim enhances the sealing effect against the nostril opening of the overall profile of the holder member, such that the holder member is securely held in place in an essentially air-tight manner in the nostril opening. Further, preferably the rim will provide air-tight sealing of the outside of the nasal device against the nostril opening when the user inhales, due to the lowered air pressure in the nostrils.

The nasal device as described in any of the nasal devices as described herein may further be manufactured in number of ways. Non-limiting examples of manners to produce a nasal device include injection moulding, die casting, moulding, 3D-printing, extrusion moulding, blow moulding, rotational moulding, vacuum forming, etc.

One example of a mould that may be used for injection moulding to form a nasal device, e.g. the nasal device of FIG. 2, 3 or 4, is illustrated in FIG. 14a, which is a cross-sectional view of a mould 200 and resulting nasal device. A non-limiting example of such a resulting nasal device formed by e.g. injection moulding is shown in FIG. 15, which is a cross-sectional view through a plane corresponding to that of line A-A or A'-A' in e.g. FIG. 2b.

Another example of a mould that may be used for injection moulding to form a nasal device, e.g. the nasal device of FIG. 2, 3 or 4, is illustrated in FIG. 14b, which is a cross-sectional view of a mould 200 and resulting nasal device. A non-limiting example of such a resulting nasal device formed by e.g. injection moulding is shown in FIG. 16, which is a cross-sectional view through a plane corresponding to that of line A-A or A'-A' in e.g. FIG. 2f.

As seen in FIGS. 14a and 14b, a mould 200 with at least two separate parts 200a, 200b is used to form a holder member, such as the holder members 33, 43, 53, and simultaneously integrally attach a filter member 26. The holder member is also preferably formed in one piece together with the support member 32, 42, 52 (not shown) in the same mould.

A method of producing a nasal device according to any nasal device disclosed herein comprises the steps of providing a mould adapted to the desired nasal device; arranging a filter member 20, 21, 26 in the mould; and forming the nasal device by essentially filling the mould with material such that the filter member becomes integrated with the nasal device.

In one aspect, the filter member 20, 21, 26 is provided as an uncut filter member, and the mould is adapted to cut or punch out the filter when a top and bottom portion of the mould are assembled or come together in the mould, either before or during moulding. As an alternative, a filter member, pre-cut to the shape of the holder member, is placed in the mould before moulding.

Further, the method may in some aspects also comprise providing a void-shaping member 200c on the distal side of the filter member 26 in the mould before filling the mould. As is illustrated in FIG. 14b, such a void-shaping member 200c may be an integral part of the provided mould 200; however, it may also be provided as a separate member and e.g. inserted from one side of the mould before filling the mould. After forming the nasal device by filling the mould with the desired material for the nasal device, the void-filling member 200c is removed from the nasal device before, simultaneously as or after removing the nasal device from the mould. As may be seen in FIG. 16, this creates a void 101 between the filter member 26 and the inside of the rounded distal portion 5.

The resulting nasal device, as seen in FIG. 16, will thus comprise a holder member 33, 43, 53 with a distal portion 5 having one or more through-going access holes 100 arranged essentially in a direction perpendicular to a distal-proximal extension, and an inner void 101 between the filter member and inner surface of the distal end 5. The access hole 100 is, as described above, a result of providing a void-shaping member during manufacture of the nasal device. In other words, the filter member 26 is arranged proximally of the one or more through-going access holes 100.

An advantage of providing a void 101 between the filter member 26 and the distal end 5 with through-going holes 36, 46, 56 is an enhanced flow of air due to a lowered air resistance through the nasal device, and thereby through the filter member 26. The visible access hole 100 may also make it easier for a user to distinguish an insertion direction of the nasal device.

However, enhanced flow of air may also be achieved by providing a nasal device such as shown in FIG. 15, i.e. with relatively large through-going holes 36, such that air flow through the device is minimally affected. Here the filter will be integrally connected both at the circumference of the filter member 26, and is preferably also additionally attached or integrated with the holder member's distal end essentially around every though-going hole 36. This provides for improved attachment of the filter member to the holder member.

The nasal device as described herein may further comprise a releasable substance dispersed in the material of or arranged on the surface of at least part of the nasal device. The substance may be inhaled by the user through the nasal device, and/or administered by diffusion or vaporization. The releasable substance may be mixed in the material of the nasal device itself, or coated onto all or part of the device using any known techniques. The filter member 20, 21 may be prepared before assembly by dipping in, spraying with, dropping onto or immersion in a desired substance.

The releasable substance may be arranged in one or several of the holder members, support member and filter member. The releasable substance may be a fragrance or perfume, providing a pleasant smell to the user. The substance may also be menthol or other appealing fragrance. Further, the releasable substance may be a medical compound or composition. As a further example, the releasable substance may be water or saline, to hydrate a nostril.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A nasal device, comprising
an elongated support member, and
one or two rounded holder members, each arranged at a respective end of said elongated support member, wherein said one or two holder members are each adapted to be inserted into a nostril with a distal end directed into the nostril, and a proximal end adjacent the nostril openings,
wherein said one or two rounded holder members are formed in one piece and made of a flexible material, and
said one or two rounded holder members each comprising a rounded distal portion,
an open proximal portion comprising an outer rim disposed circumferentially around an outer perimeter of said proximal portion and extending radially outward from said holder member, the outer rim being the end of the rounded holder member opposite the distal portion, and
an intermediate waist portion arranged between said distal portion and said proximal portion, said intermediate waist portion having at least one outer circumference in a plane essentially transverse to a distal-proximal direction, said at least one outer circumference being smaller than a respective largest outer circumference of at least said distal portion,
wherein said outer rim disposed circumferentially around the outer perimeter of the proximal portion is adapted to engage in an essentially airtight manner with the nostril opening around the entire circumference of the nostril opening and protrude outward from the nostril when the nasal device is arranged in a nostril, and
wherein the outer rim, proximal portion, intermediate waist portion, and rounded distal portion are connected by a continuous curved surface extending from the rounded distal portion to the outer rim and adapted to follow the profile of the nostril opening to secure the nasal device in the nostril opening such that the nasal device is secured by contact between the continuous curved surface and inner surfaces of the nostril opening.

2. The nasal device according to claim 1, wherein said at least one outer circumference of said intermediate waist portion is smaller than a respective largest outer circumference of each of said distal and proximal portions.

3. The nasal device according to claim 1, wherein said one or two rounded holder members are generally oval-shaped or elliptical in a plane essentially transverse to a distal-proximal extension.

4. The nasal device according claim 1, wherein said rounded distal portion is provided with one or more through-going holes adapted to allow air to pass through said distal portion.

5. The nasal device according to claim 1, wherein said rounded distal portion is provided with multiple through-going holes adapted to allow air to pass through said distal portion, and said multiple holes in said distal portion form a honeycomb pattern.

6. The nasal device according to claim 1, wherein said one or two rounded holder members are integrated with said support member.

7. The nasal device according to claim 6, wherein an extension of said outer rim forms said support member.

8. The nasal device according to claim 1, further comprising a filter member, arranged inside said distal portion or said intermediate waist portion such that essentially all air passing through said nasal device is directed through said filter member at least when air flows in a distal direction.

9. The nasal device according to claim 8, wherein said filter member is held in place by an inner circumferential rim extending radially inwards at said intermediate waist portion.

10. The nasal device according to claim 8, wherein said filter member is held in place by an attachment member.

11. The nasal device according to claim 8, wherein said filter member is integrally attached to said one or two rounded holder members.

12. The nasal device according to claim 8, wherein said distal portion of said one or two rounded holder members further comprise one or more through-going access holes arranged essentially in a direction perpendicular to a distal-proximal extension.

13. The nasal device according to claim 8, wherein said filter member is an electrostatic filter.

14. The nasal device according to claim 8, wherein said filter member is a mechanical filter.

15. The nasal device according to claim 1, wherein the nasal device comprises a releasable substance dispersed in the material of or arranged on the surface of at least part of the nasal device.

16. The nasal device according to claim 1, wherein the rounded distal portion has a convex shape.

17. The nasal device according to claim 1, wherein the nasal device is secured only by contact between the continuous curved surface and the inner surface of the nostril opening.

* * * * *